(12) United States Patent
Yang et al.

(10) Patent No.: US 10,810,329 B2
(45) Date of Patent: Oct. 20, 2020

(54) IN SILICO DESIGN OF PEPTIDES EQUILIBRATED IN A LIPID BILAYER WITH PARTITION FREE ENERGIES INDICATING PROBABILITY OF ANTIMICROBIAL ACTIVITY

(71) Applicant: NATIONAL TSING HUA UNIVERSITY, Hsinchu (TW)

(72) Inventors: Lee-Wei Yang, Hsinchu (TW); Jya-Wei Cheng, Hsinchu (TW); Hong-Chun Li, Hsinchu (TW); Cheng-Yu Tsai, Hsinchu (TW); Hui-Yuan Yu, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 979 days.

(21) Appl. No.: 15/239,168

(22) Filed: Aug. 17, 2016

(65) Prior Publication Data

US 2017/0061288 A1 Mar. 2, 2017

(30) Foreign Application Priority Data

Aug. 17, 2015 (TW) .............................. 104126710 A

(51) Int. Cl.
*G06F 30/20* (2020.01)
*C07K 7/08* (2006.01)
*G16C 99/00* (2019.01)

(52) U.S. Cl.
CPC ................ *G06F 30/20* (2020.01); *C07K 7/08* (2013.01); *G16C 99/00* (2019.02)

(58) Field of Classification Search
None
See application file for complete search history.

(56) References Cited

PUBLICATIONS

La Rocca, Paolo, et al. "Simulation studies of the interaction of antimicrobial peptides and lipid bilayers." Biochimica et Biophysica Acta (BBA)—Biomembranes 1462.1-2 (1999): 185-200.*

* cited by examiner

*Primary Examiner* — G Steven Vanni
(74) *Attorney, Agent, or Firm* — Birch, Stewart, Kolasch & Birch, LLP.

(57) ABSTRACT

The present invention provides an evaluating system and the use thereof for the efficacy of antimicrobial peptide, which includes the following steps: (a) constructing a peptide by a first input unit, and load the peptide into an aqueous solution for a first time for equilibration; (b) constructing a lipid bilayer by a second input unit, and load the lipid bilayer into an aqueous solution for a second time for equilibration; (c) Using a first processing unit, simulations are carried out for an aqueous system containing an equilibrated peptide from the first input unit and the equilibrated lipid bilayer from the second input unit; (d) calculating the partition free energy of the peptide by a second processing unit; (e) outputting the prediction by an output unit, wherein the output unit is connected with the first processing unit and the second processing unit.

7 Claims, 4 Drawing Sheets
Specification includes a Sequence Listing.

(a) A peptide is constructed by a first input unit, and the peptide is loaded in a aqueous for a first time to process a equilibrate reaction

(b) A lipid bilayer is constructed by a second input unit, and the lipid bilayer is loaded in a aqueous for a second time to process a equilibrate reaction

(c) A first processing unit, which is connecting with the first input unit and the second input unit, the first processing unit is conducting a molecular dynamics (MD) simulations in a aqueous with the lipid bilayer constructed by the second input unit

(d) The <Ni> which is the numbers of heavy atoms of antimicrobial peptide within a hydrophobic lipid tails and the <No> which is the average numbers of heavy atoms of antimicrobial peptide outside 4 Å of hydrophobic lipid tails during 4 ns snapshots are calculated and a partition free energy ($\Delta Gp$) is calculated by a second processing unit

(e) A predicted information- partition free energy ($\Delta Gp$) or a predited peptide activity information are outputted by an output unit, wherein the output unit is connected with the second processing unit

IN SILICO DESIGN OF PEPTIDES EQUILIBRATED IN A LIPID BILAYER WITH PARTITION FREE ENERGIES INDICATING PROBABILITY OF ANTIMICROBIAL ACTIVITY

CROSS-REFERENCE TO RELATED APPLICATIONS

This Non-provisional application claims priority under 35 U.S.C. § 119(a) on Patent Application No(s). 104126710 filed in Taiwan, Republic of China Aug. 17, 2015, the entire contents of which are hereby incorporated by reference.

FIELD OF THE INVENTION

The present invention is related to an evaluating system for an efficacy of antibiotic peptide and the use thereof, which is designed by stepwise circular reshuffling (SCR). By SCR, amino acids of known antibiotic peptides are collectively shifted in the primary sequence by one position at a time, in order to create a series of mutants. With the condition that the lengths of these mutants (or variants) are held unchanged, terminal residues can be shifted to the other end of the sequence depending on the direction of the shifting. The antibiotic activity and hemolytic activity of these peptide variants are evaluated by a computer simulation and a free energy calculation platform.

BACKGROUND OF THE INVENTION

Antibiotics can be classified into two groups. One contains secondary metabolites, produced by natural microorganisms (including bacteria, fungi, actinomyces) and able to inhibit the growth or survival of other microorganisms. The other contains chemically synthesized analogs of these metabolites. Antibiotic usually means anti-bacterial antibiotics in clinic but can also indicate antifungal and small pathogen antibiotics. Antibiotics now have been widely used and in fact abused causing a rampant spread of drug-resistant bacteria. Less and less long lasting antibiotics are there to battle against pathogen. Therefore, pharmaceutical companies have to constantly meet the pressing need to develop novel and more effective antibiotics.

According to information from FierceBiotech, the global antibiotics markets were expected to grow by a compound annual rate of 1.41% per year during 2013 to 2018. Although drug resistance problem caused some countries to partially ban antibiotics, the global market of antibiotic continues to expand for its irreplaceable medical benefit. According to the report of the Grand View Research, the global anti-infective agents market size was valued at USD 83.8 billion in 2015.

The antibiotic peptide is known as antimicrobial peptide (AMP). The length of the antibiotic peptide is 10 to 80 amino acids. Many organisms use the antibiotic peptide to fight against pathogens through mechanisms of penetrating or perforating the bacterial cell membrane, interfering their proliferation and promoting wound healing. Therefore, AMPs have the potential to gradually replace antibiotics in the near future.

Most of the AMP developments involve replacing the amino acids on known antimicrobial peptides to possibly enhance their efficacy. It takes time to evaluate the effects of such replacements experimentally. Considering that antimicrobial activity results from complicated synergy of constituent residues, changing charge, hydrophobic moment, interaction energy and contacting surface area by mutagenesis in order to improve the efficacy may as well alter other needed antimicrobial functions such as secondary structures and amphiphilicity of AMPs. It is difficult to predict (even qualitatively) the antimicrobial activity from a single point mutation without conducting experiments. Here we provide a design method and computational evaluation platform to respectively create potent variants and assess variants' efficacy from molecular dynamics simulations and partition free energy calculations.

SUMMARY OF THE INVENTION

The present invention provides an antimicrobial, hemolytic and salt-resistant polypeptides that are designed by stepwise circular reshuffling (SCR). The approach involves (A) shifting constituent residues collectively along the primary sequence of peptides to create variants of different antimicrobial efficacy, strain specificity and hemolytic activity, and (B) a computational platform to evaluate the efficacy of these AMP variants using molecular dynamics simulations and partition free energy calculations.

The present invention provides a new platform based on molecular dynamics (MD) simulations and trajectory analysis to evaluate the antimicrobial and hemolytic activities of AMPs. This specific protocol involves a "sink and surface" simulation. In the "sink and surface" simulation, the antimicrobial peptides are pulled and forced into the biological membrane. The "sink and surface" simulation shortens the simulation time, as compared with the free diffusion method, by about 10 folds. The partition free energy, $\Delta G_p$, can be calculated from the simulation trajectory and was proven to be a better physical indicator to infer the efficacy of AMPs.

Accordingly, the present invention provides an evaluating system for the efficacy of antimicrobial peptide, which includes:

(a) a first input unit, wherein the first input unit is for constructing a solvated peptide;

(b) a second input unit, wherein the second input unit is for constructing a solvated lipid bilayer;

(c) a first processing unit, which is connecting with the first input unit and the second input unit, is to perform molecular dynamics (MD) simulations for the peptide in the first input unit and the lipid bilayer in the second input unit;

(d) a second processing unit, connected with the first processing unit, is to calculate $<N_i>$ that is the moving average number of heavy atoms of the antimicrobial peptide contacting hydrophobic lipid tails and $<N_o>$ that is the moving average number of heavy atoms of the antimicrobial peptide not contacting hydrophobic lipid tails during a 4 ns window; and a partition free energy ($\Delta G_p$) is calculated based on $<N_i>$ and $<N_o>$; wherein the heavy atoms are all the non-hydrogen atoms;

(e) an output unit, connected with the second processing unit, is used for outputting predicted information including the partition free energy ($\Delta G_p$), wherein the first input unit, the second input unit, the first processing unit, the second processing unit and the output unit are operated by a computer.

A method for predicting antimicrobial efficacy of antimicrobial peptide by an in silico evaluating/prediction platform, comprises the following steps:

(a) A peptide is constructed by a first input unit, and is equilibrated in an aqueous solution for a first time;

(b) A lipid bilayer is constructed by a second input unit, and is equilibrated in an aqueous solution for a second time;

(c) a first processing unit, connecting with the first input unit and the second input unit, performs molecular dynamics (MD) simulations for the peptide in the first input unit and the lipid bilayer in the second input unit;

(d) a second processing unit, connected with the first processing unit, is to calculate <$N_i$> that is the moving average of the number of heavy atoms in the antimicrobial peptide contacting hydrophobic lipid tails and <$N_o$> that is the moving average of the number of heavy atoms in the antimicrobial peptide not contacting hydrophobic lipid tails during a 4 ns window; and a partition free energy ($\Delta G_p$) is calculated based on <$N_i$> and <$N_o$>; wherein the heavy atoms are all the non-hydrogen atoms;

(e) predicted partition free energy ($\Delta G_p$) and/or predicted peptide activity are outputted by an output unit, wherein the output unit is connected with the second processing unit.

Preferably, the conformation of the peptide is α-helix.

Preferably, the first input unit includes an equilibrated peptide initially taken from the X-ray crystallography or NMR data, or designed by a software including PyMol or Discovery Studio Visualizer; wherein the peptide is equilibrated by a simulation software that includes NAMD, VMD, AMBER and GROMACS with commonly used force field that includes CHARMM, AMBER, GROMOS and OPLS under physiological conditions.

Preferably, the second input unit includes a "CHARMM-GUI" server to build the lipid bilayer; wherein the lipid bilayer is equilibrated by a simulation software that includes NAMD, VMD, AMBER and GROMACS with commonly used force field including CHARMM, AMBER, GROMOS and OPLS under physiological conditions.

Preferably, the first processing unit uses a simulation software, which can be NAMD, VMD, AMBER and GROMACS with commonly used force field including CHARMM, AMBER, GROMOS and OPLS to equilibrate the system where the peptides from the first input unit stably insert into the lipid bilayer from the second input unit.

Preferably, the input of the second processing unit (the number of heavy atoms in the peptide contacting with lipid tails inside the membrane) is obtained from the simulation trajectory outputted from the first processing unit.

Preferably, the lipid bilayer is composed by a palmitoyloleoyl phosphatidyl choline (POPC) and/or palmitoyloleoyl-phosphatidylglycerol (POPG).

Preferably, the first time duration is a few hundred picoseconds.

Preferably, the predicted information is the antimicrobial activity of the peptide.

Preferably, the molecular dynamics (MD) simulations is to first orient the hydrophobic side of the antimicrobial peptide to face a pre-equilibrated lipid bilayer; the "sink and surface" simulation is carried out after the projections of mass centers of the peptide and lipid bilayer on the lipid bilayer's normal being positioned 35 Å apart from each other.

Preferably, in the "sink and surface" simulation, a helical peptide is pulled by a weak force to where 6 Å below the average coordinate of the phosphor atoms in the upper leaflet of the lipid bilayer and the helical peptide is held therein for several nanoseconds; afterwards, the weak restraint is released, and within 10 to 35 nanoseconds the helical peptide can float (surface) onto the membrane surface and equilibrate therein.

Preferably, the $\Delta G_p = -k_B T \ln(<N_i>/<N_o>)$ or $= -k_B T(<\ln N_i>/<\ln N_o>)$, where $k_B$ is the Boltzmann constant, T is the absolute temperature, $N_i$ is the average number of heavy atoms of antimicrobial peptide contacting hydrophobic lipid tails and the $N_o$ is the average number of heavy atoms of antimicrobial peptide that do not contact hydrophobic lipid tails; the < > symbol denotes moving averages for a 4 nanosecond window.

Preferably, in this invention, the correlation coefficient (R) of the partition free energy ($\Delta G_p$) and corresponding bactericidal activity (in terms of minimal inhibitory concentration, or MIC) is found to be larger than 0.80 ("1" represents the perfect correlation). In this series, the MIC=13.49*$\Delta G_p$−5.79.

The present invention also provides a method to predict antimicrobial efficacy of antimicrobial peptide by the aforementioned evaluation platform, which comprises the following steps:

(a) A peptide is constructed by a first input unit, and the peptide is loaded and equilibrated in an aqueous solution for a first time;

(b) A lipid bilayer is constructed by a second input unit, and the lipid bilayer is loaded and equilibrated in an aqueous solution for a second time;

(c) a first processing unit, connecting with the first input unit and the second input unit, performs molecular dynamics (MD) simulations for the peptide in the first input unit and the lipid bilayer in the second input unit;

(d) a second processing unit, connected with the first processing unit, is to calculate <$N_i$> that is the moving average of the number of heavy atoms in the antimicrobial peptide contacting hydrophobic lipid tails and <$N_o$> that is the moving average of the number of heavy atoms in the antimicrobial peptide not contacting hydrophobic lipid tails during a 4 ns window; and a partition free energy ($\Delta G_p$) is calculated based on <$N_i$> and <$N_o$>; wherein the heavy atoms are all the non-hydrogen atoms;

(e) predicted partition free energy ($\Delta G_p$) and/or predicted peptide activity are outputted by an output unit, wherein the output unit is connected with the second processing unit.

Preferably, the antimicrobial peptide is designed according to the following formula: xAP1yBP2zCn(P3vD) (formula I); wherein the x, y, z, v and n are all positive integers; and x=0~6, y=0 or 4, z=0~6, v=0~4 and n=0 or 1; wherein each of P1, P2 and P3 is -Trp-Leu-Lys-; wherein A, B and C are selected from the group of Trp, Leu and Lys, and D is Lys.

Preferably, the antimicrobial peptide is selected from the group of SEQ ID NO:2 to SEQ ID NO:13.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The FIG. 1 is the simple figure of the present invention.

The FIG. 2 is the flow chart of the molecular dynamics (MD) simulations system of the present invention.

Figure 1:
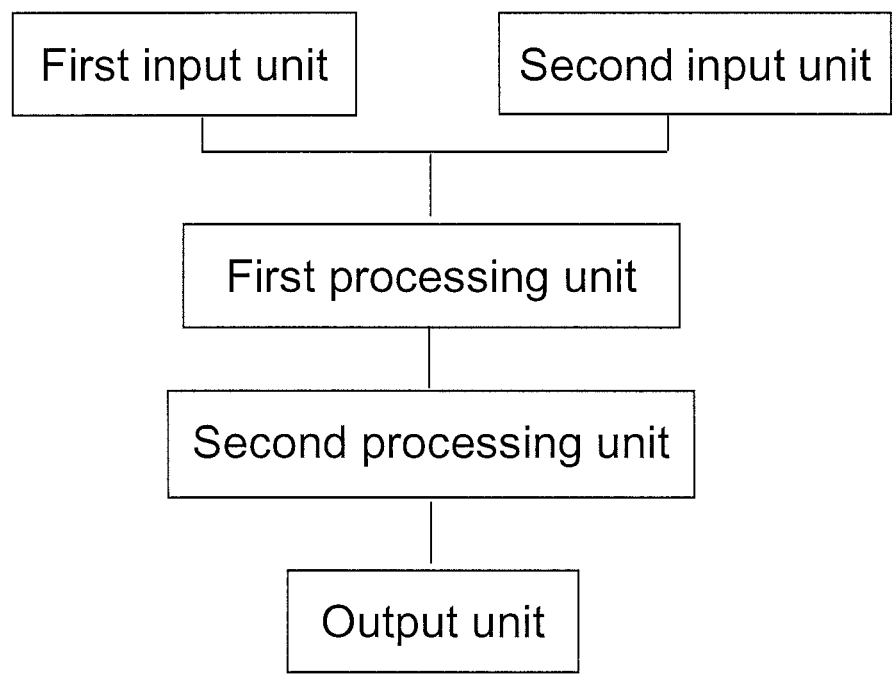
Figure 3:
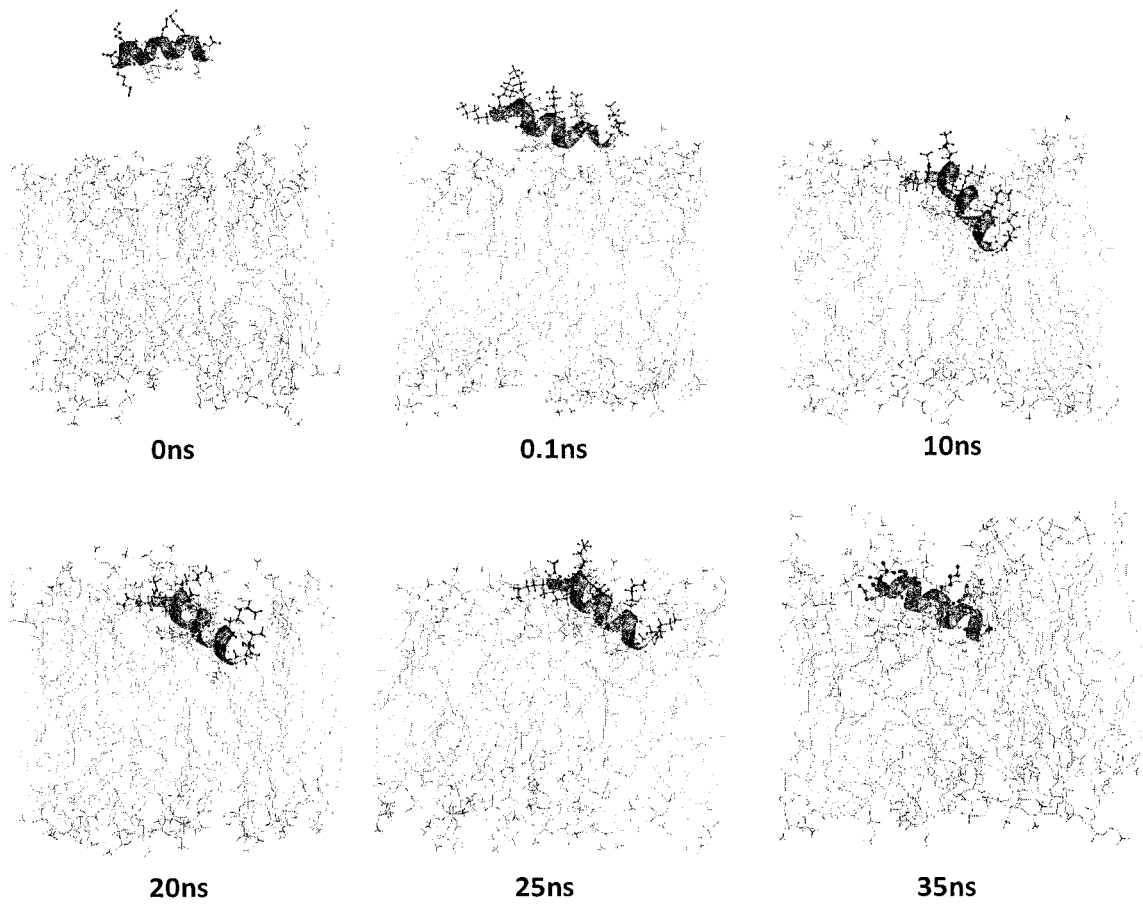

The FIG. 3 is the figure of the peptide insertion process observed in the molecular dynamics (MD) simulations system of the present invention.

Figure 4:
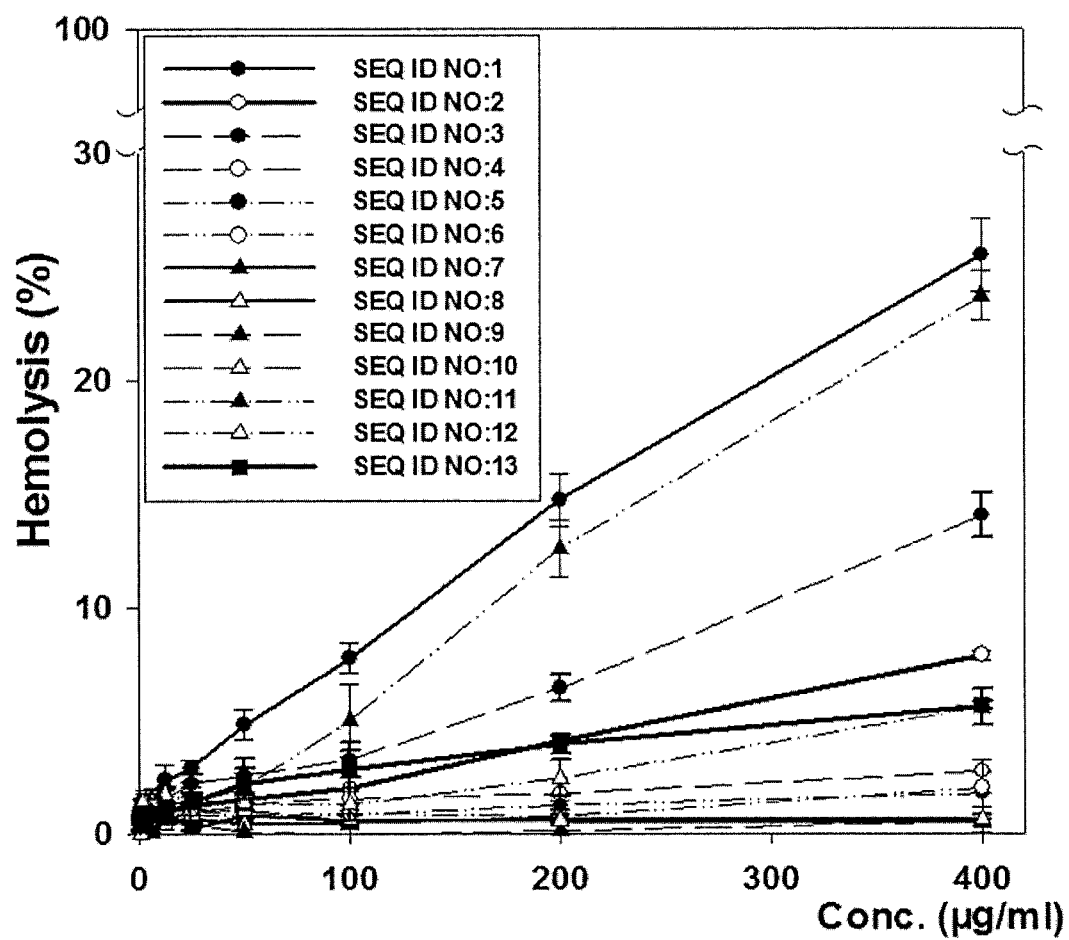

The FIG. 4 is the figure of the hemolytic activities of the present invention.

DETAILED DESCRIPTION OF THE INVENTION

For clarity of disclosure, and not by way of limitation, the detailed description of the invention is divided into the subsections that follow.

Experimental Methods:

The antimicrobial peptide of the present invention is as the following formula: $xAP1yBP2zCn(P3vD)$ (formula I); where the x, y, z, v and n are all positive integers; and $x=0~6$, $y=0$ or $4$, $z=0~6$, $v=0~4$ and $n=0$ or $1$; each of P1, P2 and P3 is -Trp-Leu-Lys-; A, B and C are selected from the group of Trp, Leu and Lys and D is Lys.

In the best embodiment, the result of molecular dynamics (MD) simulations for a series of AMP variants is shown in Table 1.

TABLE 1 the simulation results for an antimicrobial peptide family (SCR variants)

| Peptide numbers | Simulation data | | | Antimicrobial activity (MIC) (µg/ml) | |
|---|---|---|---|---|---|
| | $<Ni>$ | $<No>$ | $\Delta G_P$ (kcal/mol) | Predicted values | Experimental values |
| SEQ ID NO. 1 | 25.55 | 107.45 | 0.88 | 6.06 | 3.13 |
| SEQ ID NO. 2 | 30.03 | 102.98 | 0.75 | 4.39 | 6.25 |
| SEQ ID NO. 3 | 29.85 | 103.15 | 0.76 | 4.45 | 6.25 |
| SEQ ID NO. 4 | 17.53 | 115.48 | 1.16 | 9.80 | 12.5 |
| SEQ ID NO. 5 | 13.93 | 119.08 | 1.32 | 11.98 | 12.5 |
| SEQ ID NO. 6 | 28.70 | 104.30 | 0.79 | 4.84 | 6.25 |
| SEQ ID NO. 7 | 15.90 | 117.10 | 1.22 | 10.68 | 12.5 |
| SEQ ID NO. 8 | 22.78 | 110.23 | 0.96 | 7.21 | 6.25 |
| SEQ ID NO. 9 | 16.83 | 116.63 | 1.20 | 10.45 | 6.25 |
| SEQ ID NO. 10 | 29.68 | 103.03 | 0.76 | 4.51 | 6.25 |
| SEQ ID NO. 11 | 29.98 | 103.03 | 0.76 | 4.40 | 1.56 |
| SEQ ID NO. 12 | 37.38 | 95.63 | 0.57 | 1.94 | 1.56 |
| SEQ ID NO. 13 | 36.88 | 96.13 | 0.59 | 2.10 | 1.56 |

$\Delta G_P$ is the partition free energy.

In the best embodiment, the antimicrobial activity of the antimicrobial peptide is shown in Table 2.

MIC: Minimal Inhibitory Concentration of AMPs in MH Medium Against *E. coli* ATCC 25922

Minimal inhibitory concentration (MIC) represents for the lowest concentration of peptide at which the AMP can still kill 90% of the bacteria. All MIC tests for WLK peptide series SEQ ID NO:1-13 were measured against *Escherichia coli* strain (ATCC 25922) in triplicate. Peptide concentration was determined by UV spectrophotometer (Ultrospec 1100 pro from Amersham Biosciences) at 280 nm with proper extinction coefficient. (Gill S. C. & Von Hippel P. H., Analytical biochemistry 1989, 182(2), 319-326). All of the samples were prepared from a stock solution containing peptides of concentrations 5, 2.5, 1.25, 0.625, 0.313, 0.156 and 0.078 mg/ml. Bacteria culture in the middle of logarithmic growth at a concentration of $5\times10^5$ colony-formation unit (CFU) and protein solution at the aforementioned concentrations were uniformly mixed in a 96-well culture plate (each well contains 1 microliter protein solution and 99 microliter of bacteria culture). After growing the culture at 37° C. for 16 hours, how bacterial growth was inhibited was measured by Thermo Max (Molecular Devices) at the wavelength of 600 nm. The MIC values were determined by triplicates of the above experiments.

Hemolysis Activity Test

Hemolytic activity was determined by measuring hemolysis of human red blood cells. Fresh red blood cells and PBS buffer solution (pH 7.4) was mixed uniformly and centrifugated by relative centrifugal force (RCF) 800 g rpm for 10 minutes, washed and then diluted by the PBS buffer solution to 10% concentration by volume (v/v). All the tested peptides were prepared with different concentrations (800, 400, 200, 100, 50, 25, 12.5, 6.25, 3.13, 1.56 µg/ml) and then mixed with PBS buffer in 1:1 ratio (100 µL:100 µL) by volume. In 1:1 ratio (v/v), the red blood cell solution was mixed with a PBS buffer, with or without 2% Triton X-100, respectively as the positive and negative controls. All samples to be tested were settled at 37° C. environment for 1 hour. Next, the specimen was centrifuged under RCF 800 g for 10 minutes and the absorbance of its supernatant was measured at a wavelength of 450 nm. The hemolytic activity would be measured according to the following formula:

"% hemolysis=$[A_{sample}-A_{PBS}]/[A_{TritonX100}-A_{PBS}]$"

TABLE 2

The hemolytic activity, salt resistance, and antimicrobial acitivity of the present invention

| AMPs | Sequence | $<\mu H>$ | MIC (µg/ml) in MH medium | MIC (µg/ml) in LYM medium | | | | |
|---|---|---|---|---|---|---|---|---|
| | | | | control | NaCl concentration (nM) | | | |
| | | | | | 50 | 100 | 200 | 300 |
| SEQ ID NO. 1 | KKWLKWLKWLKKK | 0.647 | 3.13 | 1.56 | 1.56 | 3.13 | 6.25 | 6.25 |
| SEQ ID NO. 2 | KWLKWLKWLKKKK | 0.506 | 6.25 | 1.56 | 1.56 | 6.25 | 12.5 | 12.5 |
| SEQ ID NO. 3 | WLKWLKWLKKKKK | 0.575 | 6.25 | 1.56 | 3.13 | 3.13 | 12.5 | 25 |
| SEQ ID NO. 4 | LKWLKWLKKKKKW | 0.417 | 12.5 | 1.56 | 3.13 | 3.13 | 12.5 | 50 |
| SEQ ID NO. 5 | KWLKWLKKKKKWL | 0.663 | 12.5 | 3.13 | 3.13 | 12.5 | 25 | 50 |
| SEQ ID NO. 6 | WLKWLKKKKKWLK | 0.700 | 6.25 | 1.56 | 3.13 | 6.25 | 12.5 | 25 |
| SEQ ID NO. 7 | LKWLKKKKKWLKW | 0.454 | 12.5 | 3.13 | 3.13 | 6.25 | 12.5 | 50 |
| SEQ ID NO. 8 | KWLKKKKKWLKWL | 0.682 | 6.25 | 3.13 | 3.13 | 3.13 | 6.25 | 12.5 |

TABLE 2-continued

The hemolytic activity, salt resistance, and antimicrobial acitivity of the present invention

| AMPs | Sequence | <µH> | MIC (µg/ml) in MH medium | MIC (µg/ml) in LYM medium | | | | |
|---|---|---|---|---|---|---|---|---|
| | | | | control | 50 | 100 | 200 | 300 |
| | | | | | NaCl concentration (nM) | | | |
| SEQ ID NO. 9 | WLKKKKKWLKWLK | 0.678 | 6.25 | 3.13 | 3.13 | 3.13 | 12.5 | 50 |
| SEQ ID NO. 10 | LKKKKKWLKWLKW | 0.371 | 6.25 | 3.13 | 3.13 | 3.13 | 6.25 | 25 |
| SEQ ID NO. 11 | KKKKKWLKWLKWL | 0.555 | 1.56 | 1.56 | 1.56 | 1.56 | 1.56 | 3.13 |
| SEQ ID NO. 12 | KKKKWLKWLKWLK | 0.518 | 1.56 | 1.56 | 1.56 | 3.13 | 3.13 | 3.13 |
| SEQ ID NO. 13 | KKKWLKWLKWLKK | 0.661 | 1.56 | 1.56 | 3.13 | 1.56 | 3.13 | 12.5 |

The hemolytic activity, salt resistance, and antimicrobial activity of the novelly designed 12 isomeric peptides (SEQ ID NO: 2~13) based on the original helical AMP of SEQ ID NO: 1 by the process of "stepwise circular reshuffling (SCR)" were shown in Table 2. The "sink and surface" simulation strategy and $\Delta G_p$ calculation were used to measure the antimicrobial activity, and the relationship between ($\Delta G_p$) and antimicrobial activity (demonstrated by MIC) of the 13 isomeric peptides (including the original sequence) was analyzed, wherein the correlation coefficient was found greater than 0.8 (MIC=13.50*$\Delta G_p$−5.79, R=0.84). Table 2 shows that the 13 peptides in high salt concentration still had high inhibitory effects. Besides, 3 out of 12 peptides were found to have a better antimicrobial activity than the original sequence in the present invention, wherein SEQ ID NO: 12 showed lower hemolytic activity on human erythrocytes. As a result, the current invention provides a new platform whereby a repertoire of more effective antimicrobial peptides can be rationally designed based on known antimicrobial peptides, and their bactericidal activities can be predicted by herein presented computational methods.

What is claimed is:

1. A method for predicting antimicrobial activity of peptides based on an initial peptide, the initial peptide having a plurality of amino acids, the number of the plurality of amino acids being N1, comprising in silico:

(a1) designing a plurality of peptides based on the initial peptide by stepwise circularly reshuffling, wherein the number of the plurality of designed peptides is N1−1; wherein the number of amino acids of each of the plurality of designed peptides is N1; wherein, if the first one of the amino acids is connected to the last one of the amino acids in each of the peptides, then all the resulting peptides are the same; and wherein the plurality of designed peptides are isomeric peptides;

(a2) equilibrating the designed peptides and the initial peptide in an aqueous solution for a first time;

(b) designing a lipid bilayer comprising hydrophobic lipids tails and equilibrating the lipid bilayer in the aqueous solution;

(c) conducting, for each of the designed peptides and the initial peptide individually, a molecular dynamics (MD) simulation in the aqueous solution in the presence of the equilibrated lipid bilayer;

(d) calculating: for each of the designed peptides and the initial peptide, $<N_i>$ as a moving average of the number of heavy atoms in the calculated peptide in contact with the hydrophobic lipid tails during an entire 4 ns window; $<N_o>$ as a moving average of the number of heavy atoms in the calculated peptide not in contact with the hydrophobic lipid tails during the entire 4 ns window; and a partition free energy based on $<N_i>$ and $<N_o>$; wherein the heavy atoms are all non-hydrogen atoms; and (e) outputting a set of designed peptides each having partition free energies lower than the partition free energy of the initial peptide, wherein each such lower partition free energy indicates higher probability of increased antimicrobial activity of the set of designed peptides as compared to the initial peptide.

2. The method of claim 1, wherein step (a1) comprises using PyMol or Discovery Studio Visualizer software; and the MD simulation of step (c) is conducted under physiological conditions by NAMD, VMD, AMBER or GROMACS software with a force field comprising CHARMM, AMBER, GROMOS or OPLS.

3. The method of claim 1, wherein the step (e) comprises:
(e1) comparing the partition free energies of the designed peptides with the partition free energy of the initial peptide; and
(e2) outputting the partition free energies of any designed peptides which are lower than or equal to the partition free energy of the initial peptide.

4. The method of claim 1, wherein conducting, for each of the designed peptides and the initial peptide individually, the MD simulation in step (c) comprises:
making a hydrophobic side of the conducted peptide face the equilibrated lipid bilayer;
positioning projections of mass centers of the conducted peptide and the lipid bilayer on an axis perpendicular to the lipid bilayer, wherein the mass centers of the conducted peptide and the lipid bilayer are 35 Ångstroms apart from each other;
pulling the positioned peptide by a weak force to a level a few Angstroms below an average level of phosphor atoms in an upper leaflet of the lipid bilayer;
holding the pulled peptide;
releasing the held peptide; and
making the released peptide float onto a surface of the lipid bilayer and equilibrate for 10 to 35 nanoseconds.

5. The method of claim 1, wherein, in step (d), the partition free energy is calculated based on $\Delta G_p = -k_B T \ln(<N_i>/<N_o>)$ or $\Delta G_p = -k_B T (<\ln N_i>/<\ln N_o>)$, where $\Delta G_p$ is the partition free energy, $k_B$ is the Boltzmann constant, T is the absolute temperature, $N_i$ is the number of heavy atoms in the calculated peptide that contact the hydrophobic lipid tails, $N_o$ is the number of heavy atoms in the calculated peptide that do not contact the hydrophobic lipid tails, and the $<>$ symbol denotes a moving averages during the 4 ns window.

6. A method for predicting antimicrobial activity of a peptide, comprising in silico:
(a1) designing the peptide;
(a2) equilibrating the peptide in an aqueous solution;
(b) designing and equilibrating a lipid bilayer in the aqueous solution, wherein the lipid bilayer has a plurality of hydrophobic lipid tails;
(c) conducting molecular dynamics (MD) simulation in the aqueous solution with the peptide and the lipid bilayer;
(d) calculating: $<N_i>$ as a moving average of the number of heavy atoms in the peptide in contact with hydrophobic lipid tails during an entire 4 ns window; $<N_o>$ that is moving average of the numbers of heavy atoms in the peptide not in contact with the hydrophobic lipid tails during the entire 4 ns window; and a partition free energy based on $<N_i>$ and $<N_o>$; wherein the heavy atoms are all non-hydrogen atoms; and
(e) outputting the partition free energy for the peptide, wherein relative low partition free energy correlates with increased antimicrobial activity.

7. The method of claim 6, wherein step (c) includes:
making a hydrophobic side of the peptide face the equilibrated lipid bilayer;
positioning projections of a mass center of the peptide on an axis perpendicular to the equilibrated lipid bilayer, wherein the mass center of the peptide and the lipid bilayer are 35 Ångstroms apart from each other;
pulling the peptide by a weak force to a level a few Angstroms below an average level of phosphor atoms in an upper leaflet of the lipid bilayer;
holding the pulled peptide;
releasing the held peptide; and
making the released peptide float onto a surface of the lipid bilayer and equilibrate 10 to 35 nanoseconds.

* * * * *

SEQUENCE LISTING

```
<160> NUMBER OF SEQ ID NOS: 13

<210> SEQ ID NO 1
<211> LENGTH: 13
<212> TYPE: PRT
<213> ORGANISM: Artificial Sequence
<220> FEATURE:
<223> OTHER INFORMATION: helical AMP

<400> SEQUENCE: 1

Lys Lys Trp Leu Lys Trp Leu Lys Trp Leu Lys Lys Lys
1               5                   10

<210> SEQ ID NO 2
<211> LENGTH: 13
<212> TYPE: PRT
<213> ORGANISM: Artificial Sequence
<220> FEATURE:
<223> OTHER INFORMATION: isomeric peptides  based on the original
      helical AMP

<400> SEQUENCE: 2

Lys Trp Leu Lys Trp Leu Lys Trp Leu Lys Lys Lys Lys
1               5                   10

<210> SEQ ID NO 3
<211> LENGTH: 13
<212> TYPE: PRT
<213> ORGANISM: Artificial Sequence
<220> FEATURE:
<223> OTHER INFORMATION: isomeric peptides  based on the original
      helical AMP

<400> SEQUENCE: 3
```

Trp Leu Lys Trp Leu Lys Trp Leu Lys Lys Lys Lys
1               5                   10

<210> SEQ ID NO 4
<211> LENGTH: 13
<212> TYPE: PRT
<213> ORGANISM: Artificial Sequence
<220> FEATURE:
<223> OTHER INFORMATION: isomeric peptides  based on the original
      helical AMP

<400> SEQUENCE: 4

Leu Lys Trp Leu Lys Trp Leu Lys Lys Lys Lys Trp
1               5                   10

<210> SEQ ID NO 5
<211> LENGTH: 13
<212> TYPE: PRT
<213> ORGANISM: Artificial Sequence
<220> FEATURE:
<223> OTHER INFORMATION: isomeric peptides  based on the original
      helical AMP

<400> SEQUENCE: 5

Lys Trp Leu Lys Trp Leu Lys Lys Lys Lys Trp Leu
1               5                   10

<210> SEQ ID NO 6
<211> LENGTH: 13
<212> TYPE: PRT
<213> ORGANISM: Artificial Sequence
<220> FEATURE:
<223> OTHER INFORMATION: isomeric peptides  based on the original
      helical AMP

<400> SEQUENCE: 6

Trp Leu Lys Trp Leu Lys Lys Lys Lys Trp Leu Lys
1               5                   10

<210> SEQ ID NO 7
<211> LENGTH: 13
<212> TYPE: PRT
<213> ORGANISM: Artificial Sequence
<220> FEATURE:
<223> OTHER INFORMATION: isomeric peptides  based on the original
      helical AMP

<400> SEQUENCE: 7

Leu Lys Trp Leu Lys Lys Lys Lys Trp Leu Lys Trp
1               5                   10

<210> SEQ ID NO 8
<211> LENGTH: 13
<212> TYPE: PRT
<213> ORGANISM: Artificial Sequence
<220> FEATURE:
<223> OTHER INFORMATION: isomeric peptides  based on the original
      helical AMP

<400> SEQUENCE: 8

Lys Trp Leu Lys Lys Lys Lys Trp Leu Lys Trp Leu
1               5                   10

<210> SEQ ID NO 9
<211> LENGTH: 13
<212> TYPE: PRT
<213> ORGANISM: Artificial Sequence

```
<220> FEATURE:
<223> OTHER INFORMATION: isomeric peptides based on the original
      helical AMP

<400> SEQUENCE: 9

Trp Leu Lys Lys Lys Lys Lys Trp Leu Lys Trp Leu Lys
1               5                   10

<210> SEQ ID NO 10
<211> LENGTH: 13
<212> TYPE: PRT
<213> ORGANISM: Artificial Sequence
<220> FEATURE:
<223> OTHER INFORMATION: isomeric peptides based on the original
      helical AMP

<400> SEQUENCE: 10

Leu Lys Lys Lys Lys Lys Trp Leu Lys Trp Leu Lys Trp
1               5                   10

<210> SEQ ID NO 11
<211> LENGTH: 13
<212> TYPE: PRT
<213> ORGANISM: Artificial Sequence
<220> FEATURE:
<223> OTHER INFORMATION: isomeric peptides based on the original
      helical AMP

<400> SEQUENCE: 11

Lys Lys Lys Lys Lys Trp Leu Lys Trp Leu Lys Trp Leu
1               5                   10

<210> SEQ ID NO 12
<211> LENGTH: 13
<212> TYPE: PRT
<213> ORGANISM: Artificial Sequence
<220> FEATURE:
<223> OTHER INFORMATION: isomeric peptides based on the original
      helical AMP

<400> SEQUENCE: 12

Lys Lys Lys Lys Trp Leu Lys Trp Leu Lys Trp Leu Lys
1               5                   10

<210> SEQ ID NO 13
<211> LENGTH: 13
<212> TYPE: PRT
<213> ORGANISM: Artificial Sequence
<220> FEATURE:
<223> OTHER INFORMATION: isomeric peptides based on the original
      helical AMP

<400> SEQUENCE: 13

Lys Lys Lys Trp Leu Lys Trp Leu Lys Trp Leu Lys Lys
1               5                   10
```